(12) United States Patent
Schucker

(10) Patent No.: US 8,088,958 B2
(45) Date of Patent: Jan. 3, 2012

(54) METHODS FOR RECOVERY OF ALCOHOLS FROM DILUTE AQUEOUS ALCOHOL FEED STREAMS

(75) Inventor: Robert C. Schucker, The Woodlands, TX (US)

(73) Assignee: Trans Ionics Corporation, The Woodlands, TX (US)

( * ) Notice: Subject to any disclaimer, the term of this patent is extended or adjusted under 35 U.S.C. 154(b) by 444 days.

(21) Appl. No.: 12/423,452

(22) Filed: Apr. 14, 2009

(65) Prior Publication Data

US 2009/0259078 A1    Oct. 15, 2009

Related U.S. Application Data

(60) Provisional application No. 61/044,799, filed on Apr. 14, 2008.

(51) Int. Cl.
*C07C 29/86* (2006.01)
(52) U.S. Cl. .................................................. 568/918
(58) Field of Classification Search ............... 568/918
See application file for complete search history.

(56) References Cited

U.S. PATENT DOCUMENTS

| | | | | |
|---|---|---|---|---|
| 4,692,432 A | * | 9/1987 | Tedder | 568/916 |
| 6,861,248 B2 | * | 3/2005 | Dale et al. | 435/255.2 |

\* cited by examiner

*Primary Examiner* — Sikarl Witherspoon
(74) *Attorney, Agent, or Firm* — Winstead PC

(57) ABSTRACT

Methods for recovery of at least one alcohol from dilute aqueous alcohol feed streams are described. The methods include steps of a) providing a source of a dilute aqueous alcohol feed stream including at least one alcohol; b) substantially removing any solids from the dilute aqueous alcohol feed stream to form a feed stream substantially devoid of solids; c) circulating the feed stream substantially devoid of solids through a liquid-liquid extraction system having multiple equilibrium stages; d) recovering a raffinate phase substantially depleted in the at least one alcohol and an extract phase substantially enriched in the at least one alcohol; e) passing the extract phase to a recovery system wherein the extract phase is subjected to microwave radiation; f) recovering the volatilized product; and g) recycling the solvent to the liquid-liquid extraction system. The microwave radiation substantially heats the alcohol but not the solvent to form a volatilized product of substantially pure alcohol. The methods further include optional steps of removing any residual water from the substantially pure alcohol product to form a fuel-grade alcohol. The liquid-liquid extraction system can be a hydrophobic, microporous membrane extraction system having a plurality of hollow fibers.

26 Claims, 9 Drawing Sheets

METHODS FOR RECOVERY OF ALCOHOLS FROM DILUTE AQUEOUS ALCOHOL FEED STREAMS

This application claims priority to U.S. provisional patent application 61/044,799 filed Apr. 14, 2008, which is incorporated by reference herein in its entirety.

BACKGROUND

Under the Clean Air Act of 1990, the Environmental Protection Agency (EPA) was given the authority to set the maximum levels of certain air pollutants anywhere in the United States. Since most of these pollutants were derived from automotive exhausts, the concept of reformulated gasoline (RFG) was introduced by the EPA in order to help the cities and states with the highest levels of pollution meet the minimum requirements of the National Ambient Air Quality Standards, especially with respect to ozone concentration. Both methyl tertiary butyl ether (MTBE) and ethanol were approved as oxygenated gasoline additives for this purpose. Although domestic refiners have used MTBE for over a decade, recent studies have found MTBE to be carcinogenic and a source of groundwater contamination from leaking gasoline storage tanks. California and fifteen other states have subsequently instituted MTBE bans.

The inherent problems of MTBE as a fuel additive prompted renewed interest in ethanol for this purpose. Accordingly, Congress passed the Energy Policy Act of 2005, creating for the first time a Renewable Fuels Standard (RFS) that committed the United States to the use of ethanol as a replacement for MTBE in gasoline and established a baseline ethanol usage of 4 billion gallons in 2006. Approximately 30% of the gasoline now sold in the United States contains ethanol.

Congress subsequently passed the Energy Independence and Security Act of 2007, which sets a mandatory RFS requiring fuel producers to use at least 36 billion gallons of biofuels per year by 2022. The term biofuels includes ethanol, butanol and biodiesel but primarily refers to ethanol. Ethanol is primarily derived agriculturally from corn. In processes used today, ethanol is produced primarily from corn or sugar by fermentation of sugars or starches in either a batch or continuous process. The mash is heated prior to fermentation to eliminate harmful bacteria that would otherwise impede the fermentation process. After heating, the mash is transferred to a fermentation tank, and yeast is added to promote the production of ethanol, which typically takes 40-50 hours. The tank is agitated during fermentation by either a mechanical stirrer or by a gaseous air lift. The fermentation product is a dilute aqueous ethanol stream that is commonly called "beer", which contains up to about 16-18 percent ethanol by volume.

The use of corn as a fuel source competes with the use of corn as a food product, and present production capacity does not allow the United States to grow enough corn to meet demand for both. Accordingly, production of alcohols, including ethanol and butanol, from non-food (i.e., cellulosic) feedstocks will be required in order to meet the RFS in 2022. Future production of ethanol and butanol will require production from cellulosic feeds such as, for example, switch grass, corn stover, bagasse, tree bark and sawdust. Several routes have been proposed for the production of ethanol from cellulosic feedstocks. The first route involves enzymatic breakdown of cellulose and hemicellulose structures to form starches that can be subsequently fermented. The second route involves a thermochemical method in which the cellulosic feedstock is first gasified to produce synthesis gas (CO and $H_2$), which is then converted to ethanol or a mixture of alcohols and liquid hydrocarbons, all of which are usable as fuels. The enzymatic processes and at least some of the thermochemical processes produce "beer" in a dilute aqueous ethanol stream having only about 3-5 percent ethanol by volume.

In order to recover ethanol from dilute aqueous ethanol streams, the liquid (either with or without filtration to remove solids) is typically fed to a multi-stage distillation apparatus, which produces a primary overhead product containing about 93-95 weight percent ethanol. Higher ethanol content cannot be achieved by distillation, since ethanol and water form a binary azeotrope at 95.6 weight percent ethanol. An additional processing step is conventionally used for further water removal such as, for example, adsorption of water by zeolite molecular sieves to form a fuel-grade ethanol stream containing greater than about 99 weight percent ethanol. Both the distillation and the drying steps are extremely energy intensive processes, the energy input of which is comparable to that of the energy output achieved when the ethanol is burned as a fuel.

In view of the foregoing, there remains a need for efficient and economical methods for separation of ethanol and other alcohols from dilute aqueous alcohol feed streams, particularly those that do not require distillation to affect separation.

SUMMARY

In various embodiments, methods for recovery of at least one alcohol from dilute aqueous alcohol feed streams are disclosed. The methods include steps of a) providing a source of a dilute aqueous alcohol feed stream including at least one alcohol; b) substantially removing any solids from the dilute aqueous alcohol feed stream to form a feed stream substantially devoid of solids; c) circulating the feed stream substantially devoid of solids through a liquid-liquid extraction system having multiple equilibrium stages; d) recovering a raffinate phase substantially depleted in the at least one alcohol and an extract phase substantially enriched in the at least one alcohol; e) passing the extract phase to a recovery system in which the extract phase is subjected to microwave radiation; f) recovering the volatilized product; and g) recycling the solvent to the liquid-liquid extraction system after the at least one alcohol has been volatilized. The circulating step includes contacting the feed stream substantially devoid of solids with a solvent that has an stronger affinity for the at least one alcohol than for water. The solvent is substantially immiscible with the feed stream substantially devoid of solids for a sufficient time to transfer at least a portion of the at least one alcohol into the solvent. The microwave radiation substantially heats the at least one alcohol but not the solvent to form a volatilized product of a substantially pure alcohol. In various embodiments, the methods further include removing any residual water from the volatilized product to form fuel-grade alcohol.

Other various embodiments of methods for recovery of at least one alcohol from dilute aqueous alcohol feed streams are also disclosed. The methods include steps of: a) providing a source of a dilute aqueous alcohol feed stream comprising at least one alcohol; b) substantially removing any solids from the dilute aqueous alcohol feed stream to form a feed stream substantially devoid of solids; c) circulating the feed stream substantially devoid of solids through a hydrophobic, microporous membrane extraction system having a plurality of hollow fibers; d) recovering a raffinate phase substantially depleted in the at least one alcohol and an extract phase substantially enriched in the at least one alcohol; e) passing the extract phase to a recovery system in which the extract phase is subjected to microwave radiation; f) recovering the volatilized product; and g) recycling the solvent to the hydrophobic, microporous membrane extraction system after the at least one alcohol has been volatilized. The feed stream substantially devoid of solids is directed into the interior (lumen) of each of the plurality of hollow fibers and a solvent having a stronger affinity for alcohol than for water is directed to the exterior (shell) of each of the plurality of fibers. The circulating step is performed for a sufficient time to transfer at least a portion of the at least one alcohol from the feed stream into the solvent. The microwave radiation substantially heats the at least one alcohol but not the solvent to form a volatilized product of a substantially pure alcohol. In some embodiments, the methods further include recycling the raffinate phase for reuse in a fermentation process. In some embodiments, the methods further include removing any residual water from the volatilized product to form a fuel-grade alcohol.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
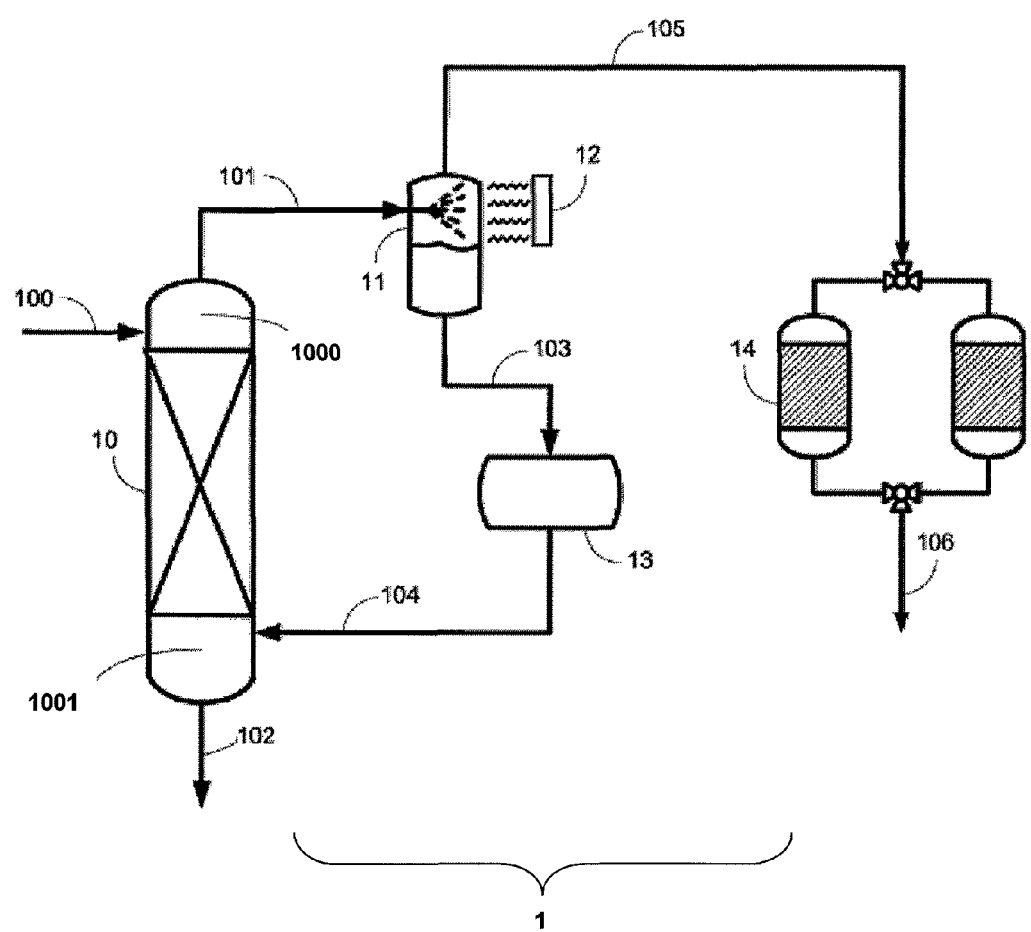
FIG. 1 presents an illustrative schematic of an apparatus used in the process for recovering fuel-grade alcohol from a dilute aqueous alcohol feed stream using a conventional liquid-liquid extraction column.

In the following description, certain details are set forth such as specific quantities, concentrations, sizes, etc. so as to provide a thorough understanding of the various embodiments disclosed herein. However, it will be apparent to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art. Reference to relative terms such as, for example, up, down, left, right, top and bottom have been made for convenience in describing the various embodiments presented herein and should not be considered limiting.

Referring to the drawings in general, it will be understood that the illustrations are for the purpose of describing particular embodiments of the disclosure and are not intended to be limiting thereto. Furthermore, drawings are not necessarily to scale.

While most of the terms used herein will be recognizable to those of ordinary skill in the art, it should be understood that when not explicitly defined, terms should be interpreted as adopting a meaning presently accepted by those of ordinary skill in the art.

In various embodiments, methods are described herein for recovery of alcohols from dilute aqueous alcohol feed streams. In various embodiments, the alcohol is ethanol. In other various embodiments, the alcohol is butanol. In various embodiments, the alcohol is a fuel-grade alcohol. Although fuel-grade alcohol primarily refers to ethanol and butanol, particularly when these alcohols are produced through a biological transformation, one of ordinary skill in the art will recognize that other various alcohols can be recovered and potentially used in fuels by utilizing embodiments of methods described herein. In general, the term "fuel-grade alcohol," as used herein, will refer to, for example, an alcohol that has an alcohol concentration greater than about 95.6 weight percent, the composition of the binary ethanol-water azeotrope. In various embodiments, fuel-grade ethanol has an ethanol concentration greater than about 96 weight percent. In some embodiments, fuel-grade ethanol has an ethanol concentration greater than about 97 weight percent. In other various embodiments, fuel-grade ethanol has an ethanol concentration greater than about 98 weight percent. In still other various embodiments, fuel-grade ethanol has an ethanol concentration greater than about 99 weight percent.

Various embodiments herein reference microwave energy or radiation. As used herein, microwave energy or radiation will be considered to reside within a frequency range of the electromagnetic spectrum between about 0.3 to about 300 GHz. In various embodiments, the microwave frequency is about 2.45 GHz. In other various embodiments, the microwave frequency is about 900 MHz (0.9 GHz).

In various embodiments, methods for recovery of at least one alcohol from dilute aqueous alcohol feed streams are disclosed. The methods include steps of a) providing a source of a dilute aqueous alcohol feed stream including at least one alcohol; b) substantially removing any solids from the dilute aqueous alcohol feed stream to form a feed stream substantially devoid of solids; c) circulating the feed stream substantially devoid of solids through a liquid-liquid extraction system having multiple equilibrium stages; d) recovering a raffinate phase substantially depleted in the at least one alcohol and an extract phase substantially enriched in the at least one alcohol; e) passing the extract phase to a recovery system in which the extract phase is subjected to microwave radiation; f) recovering the volatilized product; and g) recycling the solvent to the liquid-liquid extraction system after the at least one alcohol has been volatilized. The circulating step includes contacting the feed stream substantially devoid of solids with a solvent that has an stronger affinity for the at least one alcohol than for water. The solvent is substantially immiscible with the feed stream substantially devoid of solids for a sufficient time to transfer at least a portion of the at least one alcohol into the solvent. The microwave radiation substantially heats the at least one alcohol but not the solvent to form a volatilized product of a substantially pure alcohol. In various embodiments, the methods further include removing any residual water from the volatilized product to form a fuel-grade alcohol.

Other various embodiments of methods for recovery of at least one alcohol from dilute aqueous alcohol feed streams are also disclosed. The methods include steps of: a) providing a source of a dilute aqueous alcohol feed stream comprising at least one alcohol; b) substantially removing any solids from the dilute aqueous alcohol feed stream to form a feed stream substantially devoid of solids; c) circulating the feed stream substantially devoid of solids through a hydrophobic, microporous membrane extraction system having a plurality of hollow fibers; d) recovering a raffinate phase substantially depleted in the at least one alcohol and an extract phase substantially enriched in the at least one alcohol; e) passing the extract phase to a recovery system in which the extract phase is subjected to microwave radiation; f) recovering the volatilized product; and g) recycling the solvent to the hydrophobic, microporous membrane extraction system after the at least one alcohol has been volatilized. The feed stream substantially devoid of solids is directed into the interior (lumen) of each of the plurality of hollow fibers and a solvent having a stronger affinity for alcohol than for water is directed to the exterior (shell) of each of the plurality of fibers. The circulating step is performed for a sufficient time to transfer at least a portion of the at least one alcohol from the feed stream into the solvent. The microwave radiation substantially heats the at least one alcohol but not the solvent to form a volatilized product of a substantially pure alcohol. In some embodiments, the methods further include recycling the raffinate phase for reuse in a fermentation process. In some embodiments, the methods further include removing any residual water from the volatilized product to form a fuel-grade alcohol.

In various embodiments of the methods, the methods for recovery of the at least one alcohol are performed continuously. In other various embodiments, recovery of the at least one alcohol is performed batch-wise.

In various embodiments presented hereinabove, the methods further include removing any residual water from otherwise substantially pure alcohol to a form fuel-grade alcohol. In various embodiments, the step of removing includes treatment of the volatilized, substantially pure alcohol product with a drying agent or dessicant. In various embodiments, the step of removing includes treatment of the volatilized, substantially pure alcohol product with zeolite molecular sieves. Molecular sieve pore sizes suitable for removing water include, for example, 3 Å and 4 Å molecular sieves. Other dessicants and drying agents suitable for the step of removing residual water include, for example, silica gel, calcium sulfate, calcium chloride, sodium sulfate, magnesium sulfate and montmorillonite clay. The step of removing residual water may be conducted while the volatilized product remains in the gas phase. Optionally, the step of removing residual water may be conducted after condensing the volatilized product back to the liquid phase.

In various embodiments of the methods, the at least one alcohol separated is ethanol. In other various embodiments of the methods, the at least one alcohol separated is butanol. One of ordinary skill in the art will recognize that other alcohols may be separated by the methods described herein through appropriate modifications to the methods.

Although the concentration of the at least one alcohol in the dilute aqueous alcohol feed stream is not particularly limited, alcohol concentrations are typically less than about 20 weight percent, especially when a microbial fermentation source of the dilute aqueous alcohol feed stream is used. One of ordinary skill in the art will recognize that ethanol produced by microbial fermentation typically contains less than about 20 weight percent ethanol due to ethanol's negative effect on fermentation rates at higher concentrations. The dilute aqueous alcohol feed stream contains a concentration of alcohol of about 0.5 to about 20 weight percent alcohol in some embodiments, of about 2 to about 20 weight percent alcohol in other embodiments, of about 3 to about 20 weight percent alcohol in other embodiments, of about 3 to about 15 weight percent alcohol in some embodiments, and of about 3 to about 10 weight percent alcohol in still other embodiments. In various embodiments, a temperature of the dilute aqueous alcohol feed stream generally ranges from about 25° C. to about 100° C.

Temperature maintained in the methods for recovery of the at least one alcohol is primarily dependent on the boiling point of the extraction solvent. The extraction is performed at a temperature between about 25° C. and about 100° C. in various embodiments, between about 50° C. and about 90° C. in other embodiments, and between about 75° C. and about 80° C. in still other various embodiments.

Typically, but not always, an excess of extraction solvent is present relative to the amount of the dilute aqueous alcohol feed stream. The feed stream is substantially devoid of solids. In various embodiments, a ratio of the solvent to the feed stream substantially devoid of solids ranges from about 0.1 to about 10. In other various embodiments, a ratio of the solvent to the feed stream substantially devoid of solids ranges from about 1 to about 10. In still other various embodiments, a ratio of the solvent to the feed stream substantially devoid of solids ranges from about 1 to about 6.

Operating pressure maintained in the extraction process is not particularly critical and is generally kept high enough to retain all components in the liquid phase while the feed stream and extract are in contact. Operating pressure in the recovery system may be varied, however, to affect the rate at which the alcohol product is volatilized. For example, the pressure in the recovery system may be sub-atmospheric to enhance separation. A sub-atmospheric pressure is typically less than about 20 psia. A pressure in the recovery system ranges from about 0.01 psia to about 20 psia in various embodiments, from about 1 psia to about 15 psia in other embodiments, and from about 10 psia to about 15 psia in still other embodiments. In some embodiments, the pressure in the recovery system is about 5 to about 10 psia. Pressure and temperature in the recovery system may be optionally varied to condense the volatilized alcohol product, if desired.

In the search for more energy efficient heating means to remove extracts (alcohol extracts in the present disclosure) from extraction solvents, radiofrequency (RF) radiation (for example, microwave radiation) absorption properties of non-polar solvents have been investigated. When a solvent molecule absorbs RF radiation, heating of the solvent results. As is known to one of ordinary skill in the art, all solvents do not respond equally to microwave radiation. The leading factor that determines the extent to which a given solvent will be heated by microwave radiation is the solvent's dielectric constant (also known as permittivity). Permittivities of various solvents, alcohols and water are presented in Table 1 (reference: CRC Handbook of Chemistry and Physics, 73rd Ed., David R. Lide, Editor-in-Chief, 1992-1993). Solvents including and similar to those listed in Table 1 are among those have been used in the methods disclosed herein.

TABLE 1

Permittivities of Various Solvents

| Chemical | Permittivity ($\epsilon$) | T (° C.) |
|---|---|---|
| Water | 78.54 | 25 |
|  | 34.50 | 200 |
| Ethanol | 24.30 | 25 |
| 1-Decanol | 8.10 | 20 |
| Ethyl palmitate | 3.20 | 20 |
| Ethyl palmitate | 2.71 | 104 |
| Ethyl palmitate | 2.46 | 182 |
| Oleic Acid | 2.46 | 20 |
| Oleic Acid | 2.45 | 60 |
| Oleic Acid | 2.41 | 100 |
| p-Xylene | 2.27 | 20 |
| Isooctane | 1.94 | 20 |

In general, non-polar solvents such as, for example, those containing no heteroatoms, have relatively low permittivities. However, some solvents have heteroatoms but still maintain relatively low permittivities. Non-polar solvents may include, for example, linear alkanes, linear alkenes, branched alkanes, branched alkenes, aromatic hydrocarbons, and poly(dimethylsiloxane), also known as silicone oil. Heteroatom functionalities added to solvents that result in a polar functionality typically raise permittivity values. For example, water has an exceedingly high permittivity due to its high polarity. As indicated in Table 1, it is also of interest that the permittivity decreases with increasing temperature and also as a function of the polarity of the molecule. One of ordinary skill in the art will recognize that a wide variety of non-polar solvents may be used in the methods disclosed herein, and the illustrative examples presented in Table 1 should not be considered limiting. Although not all the solvents that are useful in the methods disclosed herein have been listed in Table 1, it is nevertheless possible to convey a general sense for the dependence of permittivity on molecular structure and how this feature generally relates to the methods disclosed herein.

As discussed in more detail in the Experimental Examples that follow, investigation of various non-polar solvents such as, for example, silicone oil, alkanes, and xylenes demonstrated that none of these solvents were excited to a large extent (i.e., heated) by microwave radiation over relatively short exposure times. Accordingly, relatively short duration microwave irradiation of non-polar solvents containing extracted alcohols and water may be used to excite the water and alcohol but not the bulk non-polar solvent, since alcohols and water have considerably higher permittivities. Through interaction of the alcohol molecules but substantially not the solvent molecules with microwave energy, it becomes possible to efficiently heat an alcohol dissolved in an extraction solvent in order to volatilize the alcohol from the extraction solvent and to affect separation, while not substantially heating the bulk extraction solvent.

A wide variety of extraction solvents may be used in the methods described herein. In various embodiments, the extraction solvent is substantially transparent to microwave energy. By the solvent being substantially transparent to microwave energy, extracted components (alcohol and water) can be selectively excited by the microwave energy. The solvent has a boiling point in excess of about 100° C. in some embodiments, in excess of about 150° C. in other embodiments, and in excess of about 200° C. in still other embodiments.

As referenced hereinabove, solvents having substantial transparency to microwave energy typically have low polarities and polarizability. In various embodiments, the solvent includes, for example, linear alkanes, linear alkenes, branched alkanes, branched alkenes and aromatic hydrocarbons. In various embodiments, the solvent is poly(dimethylsiloxane). Illustrative examples of solvents useful in the methods include, but are not limited to, saturated aliphatic hydrocarbons, including linear and branched alkanes, having carbon numbers from about 8 to about 20. Illustrative examples of saturated aliphatic hydrocarbons include, for instance, octane, dodecane and hexadecane. Alternatively, the solvent may be an olefinic hydrocarbon, including linear and branched alkenes, having carbon numbers from about 8 to about 20. Illustrative examples of olefinic hydrocarbons include, for instance, 1-octene, 1-decene and 1-dodecene. The solvent may be an aromatic hydrocarbon such as, for example, xylenes and 1-methylnaphthalene. Alternatively, the solvent may be a silicone oil, as exemplified by Dow Corning 200 series of poly(dimethylsiloxane) oligomers. The extraction solvent may be a liquid or solid at room temperature. Extraction solvents which are solid at room temperature may be liquefied by warming to a temperature below their boiling point before initiating the extraction process. Extraction solvents which have higher boiling points may be more useful for separating alcohols which have higher boiling points.

The extraction solvent may be a pure material or a mixture. In embodiments wherein the extraction solvent is a mixture, the extraction solvent may be modified by the addition of materials that are slightly more polar than the bulk extraction solvent and have a strong affinity for extraction of alcohols. In some embodiments, the added materials absorb microwave radiation, and in other embodiments, they are microwave transparent. In various embodiments, the solvent includes a non-polar primary component and a polar modifier. The non-polar primary component is substantially microwave transparent. The polar modifier improves extraction of the at least one alcohol and more efficiently absorbs microwave radiation than the non-polar primary component. In various embodiments, the non-polar primary component includes, for example, linear alkanes, linear alkenes, branched alkanes, branched alkenes and aromatic hydrocarbons. In various embodiments, the non-polar primary component is poly(dimethylsiloxane).

In various embodiments, polar modifiers include, for example, long chain alcohols, long chain fatty acids, esters of long chain fatty acids, and ethers. Illustrative long chain alcohols include, for example, 1-dodecanol, cetyl alcohol and stearyl alcohol. Illustrative long chain fatty acids include, for example, oleic acid, linoleic acid and linolenic acid. Illustrative esters of long chain fatty acids include, for example, methyl oleate and mixtures substantially derived from biodiesel. In various embodiments, the polar modifier is derived from naturally-occurring triglycerides, oils and fats. Illustrative examples include, but are not limited to, corn oil, soybean oil, olive oil and castor oil. The amount of polar modifier may be greater than about 1 weight percent of the solvent in some embodiments, greater than about 50 weight percent of the solvent in other embodiments, and greater than about 90 weight percent of the solvent in still other embodiments. In some embodiments, the polar modifier forms about 1 to about 99 weight percent of the solvent. In some embodiments, the polar modifier forms about 5 to about 90 weight percent of the solvent. In some embodiment, the polar modifier forms about 25 to about 75 weight percent of the solvent. In all cases, the non-polar primary component forms the remainder of the extraction solvent mixture. In choosing an extraction solvent mixture, a primary guideline for choice of the solvent composition is the degree to which the solvent mixture absorbs microwave radiation.

In the discussion that follows, embodiments of apparatuses for separating at least one alcohol from a dilute aqueous alcohol feed stream are described in some detail. However, the embodiments described hereinbelow should not be considered limiting. FIG. 1 presents an illustrative schematic of an apparatus 1 used in the process for recovering fuel-grade alcohol from a dilute aqueous alcohol feed stream using a conventional liquid-liquid extraction column. As shown in FIG. 1, a dilute aqueous alcohol feed stream enters apparatus 1 through line 100. In various embodiments, the dilute aqueous alcohol feed stream is a dilute aqueous ethanol feed stream from a fermentation reactor, which generally is maintained at a temperature between about 25° C. to about 40° C. In some embodiments, a heat exchanger (not shown) is used to reduce the temperature of the dilute aqueous alcohol feed stream to a temperature desired for extraction. In other embodiments, a heater (not shown) is used to heat the dilute aqueous alcohol feed stream to a temperature desired for extraction. In some embodiments, extraction is performed at a temperature between about 25° C. and about 100° C. In other embodiments, extraction is performed at a temperature between about 50° C. and about 90° C. In still other various embodiments, extraction is performed at a temperature between about 75° C. and about 80° C.

According to the embodiment presented in FIG. 1, extraction is carried out in a conventional liquid-liquid extraction vessel 10 [W. L. McCabe and J. C. Smith, *Unit Operations in Chemical Engineering*, 2nd Ed., McGraw-Hill Book Company, New York, N.Y., 1967]. In various embodiments, the liquid-liquid extraction vessel 10 can include at least one of, for example, a mixer-settler, a spray column, a packed column, a perforated plate column, a baffled column, an agitated column, a centrifugal contactor, a membrane contactor, and combinations thereof. The design and functions of these components will be understood by one of ordinary skill in the art. In various embodiments, membrane contactors include a plurality of hollow fibers. In various embodiments, a feed stream that is substantially devoid of solids is fed into the interior (lumen) of each of the plurality of hollow fibers and the solvent is fed to the exterior (shell) of each of the plurality of hollow fibers. The more dense dilute aqueous alcohol feed stream enters the top of extraction vessel 10 through line 100, and the dilute aqueous alcohol feed stream progresses downward through the column within extraction vessel 10 before exiting through line 102. Meanwhile, a less dense extraction solvent enters the bottom of extraction vessel 10 through line 104 and progresses upward through the column within extraction vessel 10 before exiting through line 101.

Extraction vessel 10 further contains means for enhancing contact between the dilute aqueous alcohol feed stream and the extraction solvent. For example, the extraction vessel can include such features as sieve trays (not shown), baffles (not shown), agitators (not shown), disengaging zones 1000 and 1001, and combinations thereof. Disengaging zones 1000 and 1001 enhance effective separation of the aqueous and extraction solvent phases to allow for efficient recovery of each phase. Following extraction, there are obtained a raffinate phase that is substantially depleted in alcohol and an extract phase that is substantially enriched in alcohol.

The raffinate phase in line 102 may be recycled to, for example, a fermentation reactor in order to conserve water usage, since the raffinate phase is substantially reduced in alcohol content. The extract phase exits extraction vessel 10 through line 101 and is then fed to flash drum 11, which has an associated a microwave source 12 that directs microwave radiation to the extract phase in flash drum 11. In some embodiments, the extract phase is sprayed into flash drum 11 through a plurality of spray nozzles (not shown) to produce a fine spray of extract droplets. Through choice of a solvent that does not interact substantially with microwave radiation, the microwave radiation emitted from microwave source 12 heats almost exclusively the extracted alcohol such as, for example ethanol, but substantially not the bulk extraction solvent. Upon heating, the alcohol volatilizes from flash drum 11 and exits through line 105. A small amount of residual water retained from the extraction process may also be volatilized at this time. Solvent from which alcohol has been removed exits flash drum 11 as a liquid through line 103 and enters surge tank 13. From surge tank 13, the solvent may optionally be heated or cooled and recycled to extraction vessel 10 through line 104. Alcohol vapors exiting through line 105 may be further dried, if necessary, by passing the alcohol vapors through drying column 14. The drying column 14 may contain a drying agent such as, for example, molecular sieves or any of other drying agents mentioned hereinabove or known to those of ordinary skill in the art. More than one drying column 14 may be used in parallel. After drying, a fuel grade alcohol stream exits apparatus 1 through line 106. Apparatus components such as, for example, pumps and heat exchangers, which are commonly used in extraction systems, have been omitted for clarity. However, one of ordinary skill in the art will recognize that these components can be included as needed while still operating within the spirit and scope of the present disclosure. In various embodiments, the apparatus includes an optional distillation module downstream of line 106 to separate any carryover solvent evaporated during microwave heating.

Figure 2:
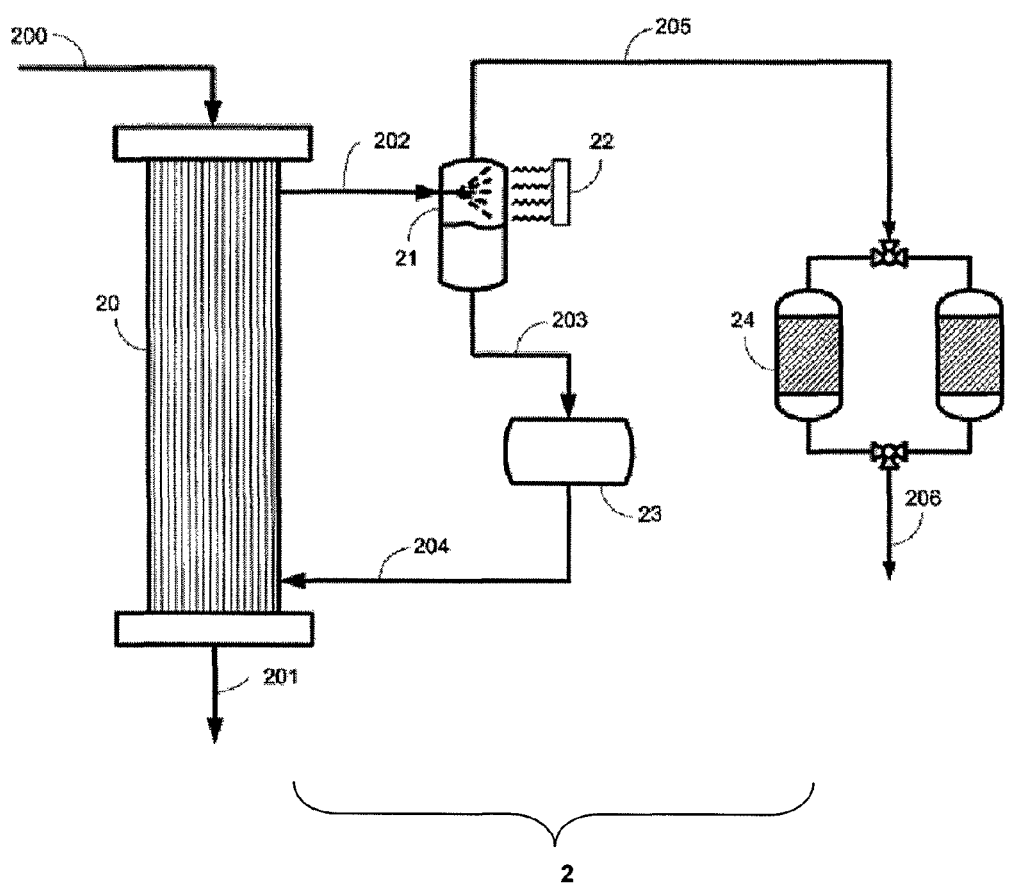
FIG. 2 presents an illustrative schematic of an apparatus having a membrane contactor and including a plurality of hollow fibers, which is used in the process for recovering fuel-grade alcohol from a dilute aqueous alcohol feed stream.
Figure 3:
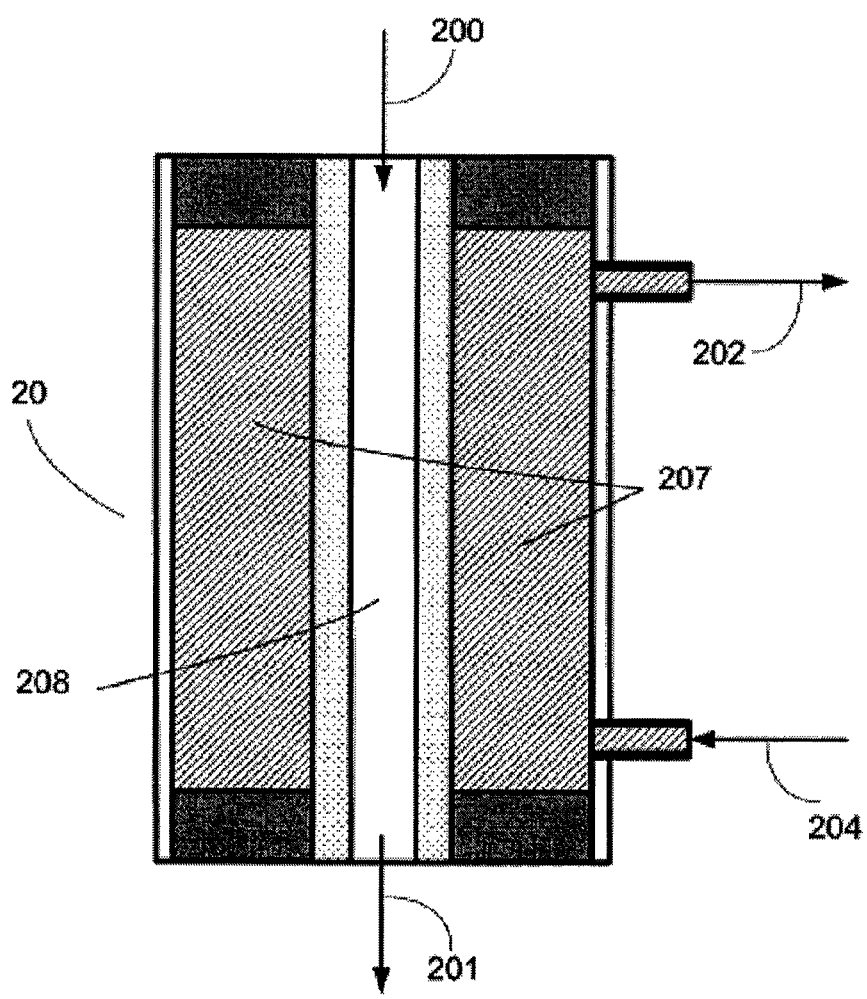
FIG. 3 presents an expanded view of the apparatus shown in FIG. 2, in which an illustrative schematic of an individual hollow fiber in the membrane contactor is shown.

One of the reasons that liquid-liquid extraction has not been more commonly adopted for solvent recovery is due to the energy consumption and capital costs associated with removing the extracted material from the solvent. Instead, distillation has more traditionally been used, wherein a typically lower boiling extract is recovered overhead and a higher boiling extraction solvent is recovered as the still bottoms. A significant economic disadvantage of distillation is that a significant amount of heat energy is expended to "boil up" the solvent, making the energy consumption quite high. This disadvantage is somewhat overcome if the extraction solvent to feed stream ratio is relatively low. In the case of dilute aqueous alcohol feed streams, such as those described in the present disclosure, the relatively high extraction solvent to feed stream ratio makes distillation-based separation relatively economically infeasible, as discussed hereinabove FIG. 2 presents an illustrative schematic of an apparatus 2 having a membrane contactor 20 and including a plurality of hollow fibers, which is used in the process for recovering fuel grade alcohol from a dilute aqueous alcohol feed stream. As shown in FIG. 2, a dilute aqueous alcohol feed stream enters apparatus 2 through line 200. Alcohol weight percent compositions and temperature of the dilute aqueous alcohol feed stream are within the ranges set forth hereinabove. After passing through line 200, extraction is carried out in membrane contactor 20. Membrane contactor 20 includes a plurality of hollow fibers in which the extraction process takes place. FIG. 3 presents an expanded view of the apparatus shown in FIG. 2, in which an illustrative schematic of an individual hollow fiber in the membrane contactor is shown. One of ordinary skill in the art will recognize that many different contactor types and flow configurations may be used to carry out the extraction process while still operating within the spirit and scope of the present disclosure.

Referring to FIGS. 2 and 3, the dilute aqueous alcohol feed stream enters membrane contactor 20 through line 200 and progresses into the interior of each of the plurality of hollow fibers (i.e., the fiber lumen 208). The dilute aqueous alcohol feed stream thereafter progresses downward through the hollow fibers in membrane contactor 20 before exiting through line 201. Meanwhile, an extraction solvent enters membrane contactor 20 through line 204 and progresses upward while passing on the exterior surface of each of the plurality of hollow fibers (i.e., the fiber shell 207) before exiting through line 202. The fibers are permeable to the alcohol in the dilute aqueous alcohol feed stream, and diffusion of the alcohol occurs from the dilute aqueous feed stream in lumen 208 into the extraction solvent outside of fiber shell 207 in order to affect extraction. A continuous concentration gradient is maintained by flowing the extraction solvent.

The raffinate phase in line 201 may be recycled to, for example, a fermentation reactor in order to conserve water usage, since the raffinate phase is substantially reduced in alcohol content. The extract phase in line 202 is then fed to flash drum 21, which has an associated microwave source 22 that directs microwave radiation to the extract phase in flash drum 21. In various embodiments, the extract phase is sprayed into flash drum 21 through a plurality of spray nozzles (not shown) to produce a fine spray of extract droplets. Microwaves emitted from microwave source 22 heat almost exclusively the alcohol (ethanol, for example) but substantially not the extraction solvent. Upon heating, the alcohol volatilizes from flash drum 21 and exits through line 205. Solvent from which alcohol has been removed exits flash drum 21 as a liquid through line 203 and enters surge tank 23. From surge tank 23, the solvent may optionally be heated or cooled and recycled to membrane contactor 20 through line 204. Alcohol vapors exiting through line 205 may be further dried, if necessary, by passing the alcohol vapors through drying column 24. The drying column 24 may contain a drying agent such as, for example, molecular sieves or any other drying agent mentioned hereinabove or known to those of ordinary skill in the art. More than one drying column 24 may be used in parallel. After drying, a fuel-grade alcohol stream exits apparatus 2 through line 206. Apparatus components such as, for example, pumps and heat exchangers, which are commonly used in extraction systems have been omitted for clarity. However, one of ordinary skill in the art will recognize that these components can be included as needed while still operating within the spirit and scope of the present disclosure. In various embodiments, the apparatus includes an optional distillation module downstream of line 206 to separate any carryover solvent evaporated during microwave heating.

Several advantages are realized through the above described methods and apparatuses for recovery of fuel-grade alcohol. For example, the use of standard solvent extractor configurations simplifies the commercial implementation of this process, since such extractors are commonly used in petroleum refineries and chemical plants worldwide today. Furthermore, such extractors are considerably cheaper than distillation apparatuses, since they need not be made of stainless steel. The use of a membrane contactor, especially a hollow fiber membrane contactor, provides a large area for interfacial transport without physically mixing the dilute aqueous alcohol feed stream and the extraction solvent, thereby eliminating the formation of emulsions and permitting the use of two immiscible liquids of comparable densities. Similar use is not possible in conventional liquid-liquid extraction systems, since gravity settling is used to separate the two liquids. Of far more significance, however, only the extracted alcohol is substantially heated by the microwave radiation, and the processes disclosed herein advantageously use far less energy than do distillation processes. Accordingly, a larger extraction solvent to feed stream ratio may be employed than if the entire extract stream had to be heated as in a conventional distillation. The methods disclosed herein may therefore provide fuel-grade ethanol by more economical means than are currently available. However, the methods are not limited to the extraction of ethanol. Butanol and other alcohols made by fermentation may also be effectively separated using the methods of the present disclosure.

EXAMPLES

The following experimental examples are included to demonstrate particular aspects of the present disclosure. It should be appreciated by those of skill in the art that the methods described in the examples that follow merely represent exemplary embodiments of the disclosure. Those of skill in the art should, in light of the present disclosure, appreciate that many changes can be made in the specific embodiments described and still obtain a like or similar result without departing from the spirit and scope of the present disclosure.

Example 1

Microwave Heating of Various Solvents

Solvents shown in Table 2 were selected and tested for their propensity to be heated by microwave radiation. EXXAL™ 13 and ISOPAR™ M are registered trademarks of the ExxonMobil Corporation. Descriptions of these materials follow in Table 2.

TABLE 2

Solvents used in Microwave Heating Experiments

| Solvent Name | Solvent Description | Boiling Point (° C.) |
|---|---|---|
| EXXAL ™ 13 | Tridecyl alcohol | 250-270 |
| ISOPAR ™ M | Isoparaffinic hydrocarbon | 218-257 |
| Mixed Xylenes | Mixture of $C_8$ Aromatics | 138-140 |
| 1-Methylnaphthalene | $C_{11}$ Aromatic hydrocarbon | 240-243 |

Figure 4:
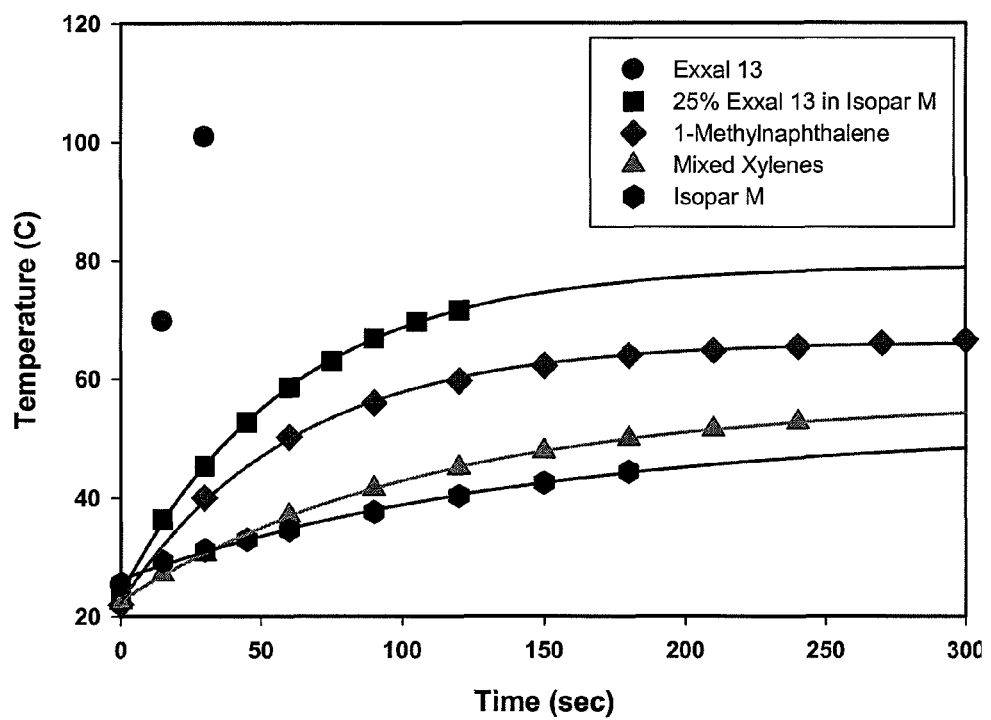
FIG. 4 presents illustrative plots of the microwave heating curves as a function of heating time for the solvents shown in Table 2.

In order to evaluate how well microwave radiation heated the individual solvents in Table 2, the solvents were subjected to 15 second intervals of heating in a GE microwave oven (GE Model JES738WJ02). After heating, the temperature was quickly measured and the sample was placed back in the microwave oven for additional heating. FIG. 4 presents an illustrative plot of the microwave heating curves as a function of heating time for the various solvents shown in Table 2.

As can be seen from FIG. 4, ISOPAR™ M, a nonpolar isoparaffinic hydrocarbon solvent, was only slightly heated by microwave energy after 4 minutes of irradiation. Mixed xylenes, which are only slightly more polar, were also only heated slightly by microwave irradiation. In contrast, EXXAL™ 13, a polar $C_{13}$ alcohol (tridecyl alcohol), was heated to over 100° C. in only 20 seconds. A mixture of EXXAL™ 13 and ISOPAR™ M exhibited a heating curve intermediate between the two pure materials, as expected. Each data set (with the exception of EXXAL™ 13) was further fit with an exponential curve in order to determine the maximum temperature that would be reached by each solvent. In each case, excellent curve fits were obtained, with $R^2$ values typically greater than 0.99. Maximum temperatures reached by the various solvents during microwave irradiation as predicted by the curve fitting are shown in Table 3. The listed maximum temperature for EXXAL™ 13 was determined by regression analysis and was not a measured value.

TABLE 3

Fitted Maximum Solvent Temperatures Reached During Microwave Heating

| Solvent | $T_{max}$ (° C.) |
| --- | --- |
| ISOPAR ™ M | 51.7 |
| Xylenes | 56.4 |
| 1-Methylnaphthalene | 66.3 |
| 25% EXXAL ™ 13/ISOPAR ™ M | 79.2 |
| EXXAL ™ 13 | 175.0 |

Figure 5:
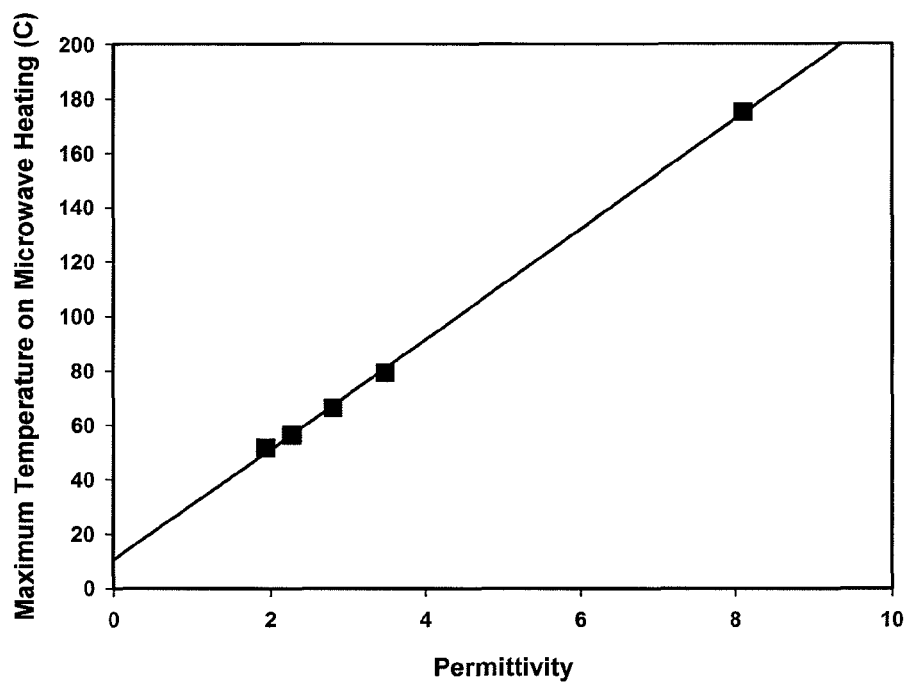
FIG. 5 presents an illustrative plot of solvent permittivity versus maximum temperature reached during microwave heating for the solvents shown in Table 3.

The maximum temperatures reached during irradiation were then correlated with the solvent permittivity (∈). Since permittivities for some of the solvents were not available, values for solvents having similar structural features were used. For example, for EXXAL™ 13, the permittivity for 1-decanol (a very similar structure) was used. FIG. 5 presents an illustrative plot of solvent permittivity versus maximum temperature reached during microwave heating. It is of particular interest that the maximum temperature for the mixture of EXXAL™ 13 and ISOPAR™ M can be predicted based upon a linear combination of the individual maxima of these two solvents.

The following examples show the utility of microwave heating for recovering ethanol from various solvents.

Example 2

Separation of Ethanol from Silicone Oil

Approximately 9.54 gm of Dow Corning DC200.20 silicone oil was added to a 50 mL polyethylene beaker. To the silicone oil was added 0.87 gm anhydrous ethanol and the mixture was stirred to homogenize. An initial weight of the beaker plus contents was then obtained. The beaker was then placed into a conventional home microwave oven (GE Model JES738WJ02) and heated for 1 minute at full power. At this point, the beaker was removed, weighed quickly and returned to the microwave oven. This process was repeated until a total of 5 minutes of heating had been conducted.

Figure 6:
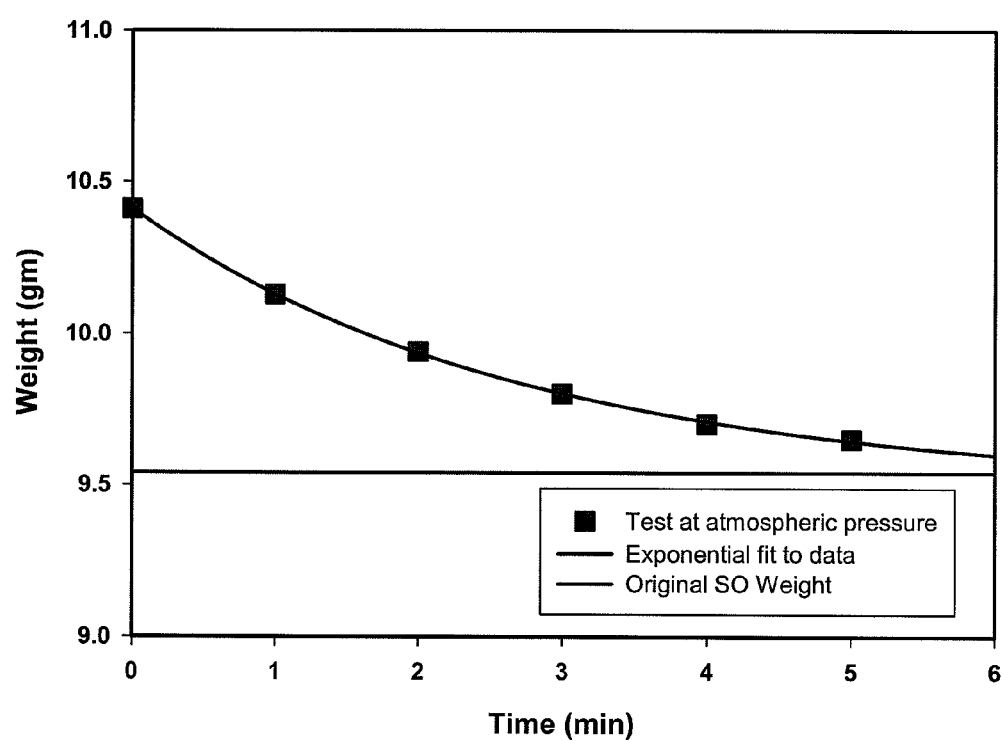
FIG. 6 presents an illustrative plot of beaker content weight (silicone oil plus ethanol) as a function of microwave heating time.

FIG. 6 presents an illustrative plot of beaker content weight (silicone oil plus ethanol) as a function of microwave heating time. Weight loss data were fit with a simple exponential decay equation. As shown in FIG. 6, total weight asymptotically approached the initial weight of the silicone oil, which indicated that substantially only ethanol was evaporated during the heating process. During the microwave irradiation, the beaker remained cool, although temperature was not actually measured in this experiment. The data indicate that microwave energy can selectively discriminate between ethanol and silicone oil during microwave heating. The data further indicate that microwave heating is capable of removing ethanol from silicone oil without heating the entire solvent mass, thus conserving energy.

Example 3

Separation of 2% Ethanol from Silicone Oil and Water

To approximately 9.80 gm of Dow Corning DC200.5 silicone oil was added 0.20 gm of a mixture of 99 wt. % anhydrous ethanol and 1 wt. % water to create a 2% mixture of hydrated ethanol in silicone oil solvent. The mixture was stirred to homogenize. Approximately 9.00 gm of this mixture were added to a 50 mL polyethylene beaker. An initial weight of the beaker plus contents was then obtained. The beaker was then placed into a conventional home microwave oven (GE Model JES738WJO2) and heated for 1 minute at full power. At this point, the beaker was removed, weighed quickly and returned to the microwave oven. This process was repeated until a total of 8 minutes of heating had been conducted.

Figure 7:
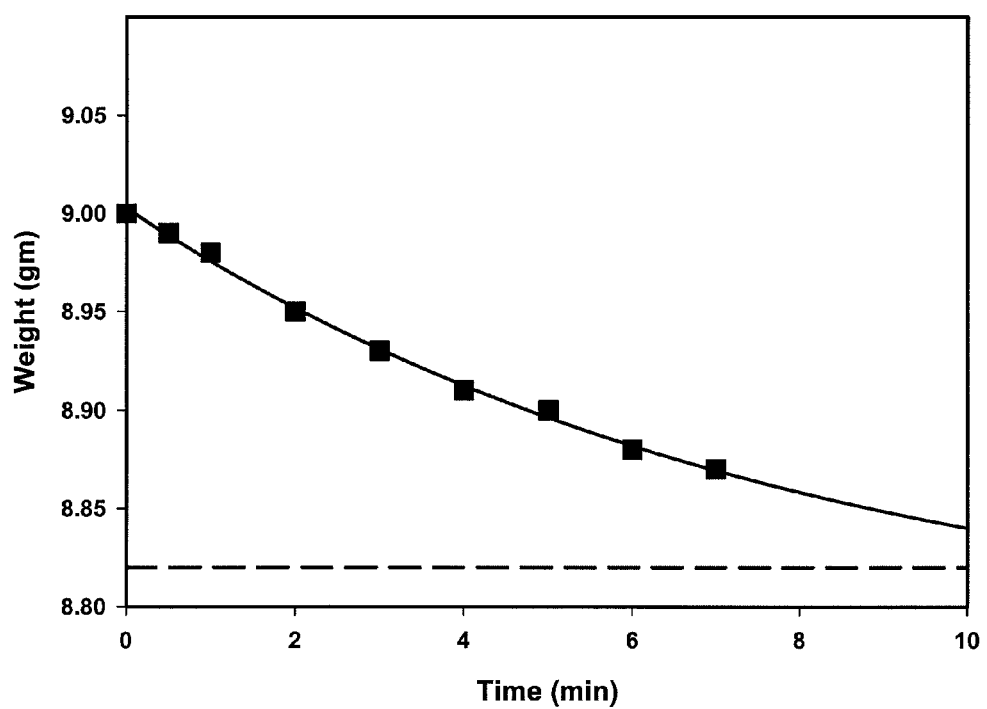
FIG. 7 presents an illustrative plot of beaker content weight (silicone oil plus 2% ethanol and water) as a function of microwave heating time.

FIG. 7 presents an illustrative plot of beaker content weight (silicone oil plus 2% ethanol and water) as a function of microwave heating time. Weight loss data were fit with a simple exponential decay equation. As shown in FIG. 7, total weight asymptotically approached the initial weight of the silicone oil, which indicated that only ethanol and water were evaporated during the heating process. The beaker remained cool during microwave irradiation and had a final temperature of only 54.8° C. as measured by a thermocouple upon completion of irradiation. The data indicate that microwave energy can selectively discriminate between ethanol/water and silicone oil during microwave heating. The data further indicate that microwave heating is capable of removing ethanol from silicone oil in the presence of small amounts of water without excessive heating of the entire solvent mass, thus conserving energy.

Example 4

Separation of 5% Ethanol from Silicone Oil and Water

Example 3 was repeated except that a 5 wt. % solution of hydrated ethanol in DC200.5 silicone oil was used. The solution was prepared using 99 wt. % anhydrous ethanol/1 wt. % water in DC200.5 silicone oil. Microwave heating was carried out in 1 minute intervals over a total of 10 minutes.

Figure 8:
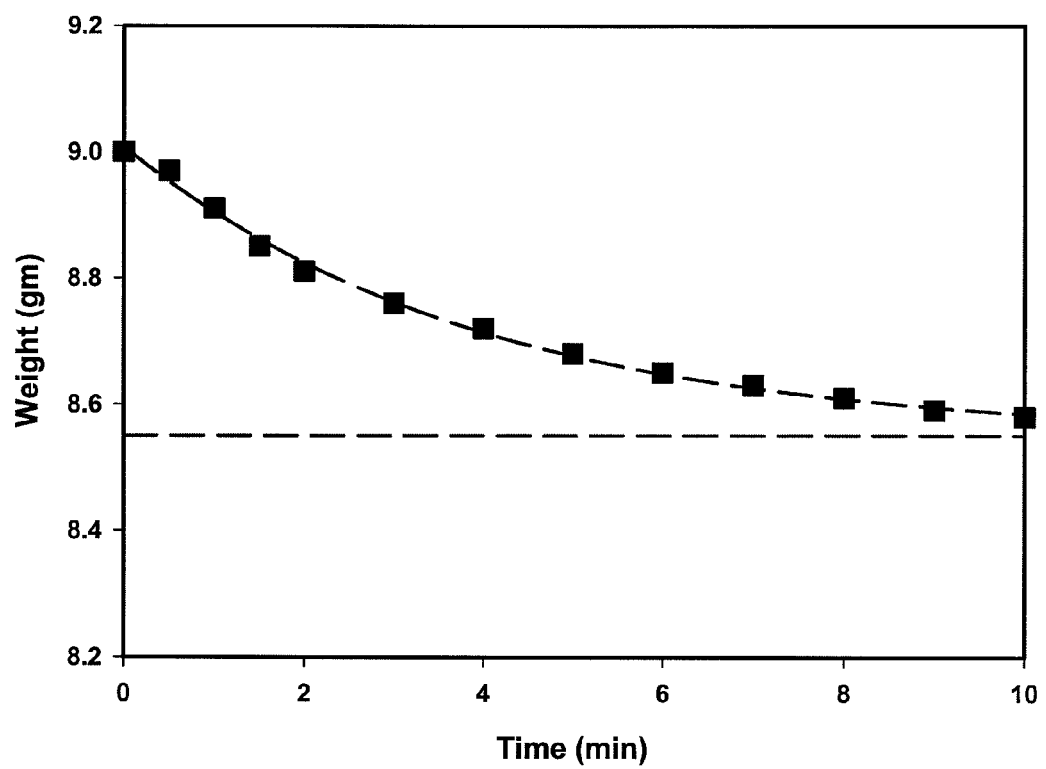
FIG. 8 presents an illustrative plot of beaker content weight (silicone oil plus 5% ethanol and water) as a function of microwave heating time.

FIG. 8 presents an illustrative plot of beaker content weight (silicone oil plus 5% ethanol and water) as a function of microwave heating time. Weight loss data were fit with a simple exponential decay equation. As shown in FIG. 8, total weight asymptotically approached the initial weight of the silicone oil, which indicated that only ethanol and water were evaporated during the heating process. Again, the data indicate that microwave energy can selectively discriminate between ethanol/water and silicone oil during microwave heating. The data further indicate that microwave heating is capable of removing ethanol from silicone oil in the presence of small amounts of water without excessive heating of the entire solvent mass, thus conserving energy.

Example 5

Separation of 2.9% Ethanol from Xylenes and Water

A test mixture containing approximately 97 wt. % xylenes, 2.9 wt. % ethanol and 0.1 wt. % water was prepared. This solvent composition was chosen based upon process simulations of the embodiments described hereinabove, which indicated that similar compositions would be obtained with xylenes solvent following liquid-liquid extraction.

Figure 9:
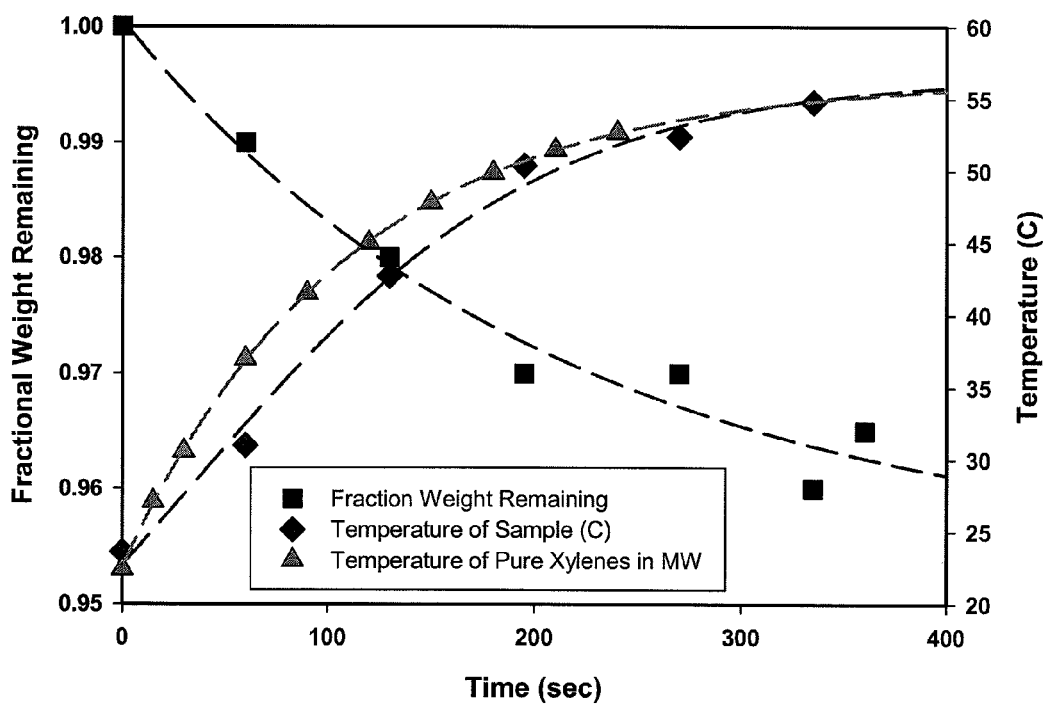
FIG. 9 presents illustrative plots of temperature and fractional weight remaining as a function of microwave heating time for a 2.9% ethanol/1% $H_2O$/97% xylenes composition.

Each test consisted of two sets of runs. In the first set of experiments, 10 mL of simulated extract was placed in a microwave-transparent (polyethylene) beaker, and the beaker was transferred to the tray of a standard GE microwave oven referenced hereinabove. The sample was heated at 100% power for 60 seconds, after which time the temperature was measured. The heating and temperature measurement steps were repeated until a total of 6 minutes of microwave heating time had elapsed. FIG. 9 presents an illustrative plot of temperature as a function of microwave heating time for this composition. As shown in FIG. 9, the temperature approached an asymptotic value of about 56° C., in agreement with the data from Example 1.

In the second series of experiments, 10 mL of the simulated extract was placed in a similar plastic beaker, and the beaker was weighed at room temperature. The beaker plus contents was then heated in 30 second increments at full microwave power. After each 30 second heating cycle, the weight was measured and the sample was quickly placed back into the microwave oven for the next heating cycle. FIG. 9 presents an illustrative plot of fractional weight remaining versus microwave heating time obtained for this composition.

Several interesting observations can be made based on the data shown in FIG. 9. First, the maximum temperature that the sample approached was almost identical to that obtained using pure mixed xylenes. This data suggests that if the ethanol and water can be removed from the extract rapidly, less heat is needs to be transferred by conduction. Since the amount of water present is below a level that generates a significant temperature increase on its own and the boiling point of ethanol is only 78° C., the bulk solvent should therefore not heat appreciably due to conductive heat transfer from the ethanol or the water.

An exponential curve fit of the weight loss data shown in FIG. 9 predicted an asymptote for fractional weight remaining of 0.954, implying that the maximum fractional weight loss of the sample would be 0.046. Since the ethanol and water formed a sample fraction of 0.03 initially, the remainder must be due to xylenes. Therefore, the vapor volatilized from the extract was ~67 wt. % ethanol/water and ~33 wt. % mixed xylenes. These values can be factored into process simulations to account for the heat necessary to volatilize the ethanol from the extract stream. The data further suggests a potential need to include a small distillation column downstream of the extract recovery system in the apparatuses disclosed hereinabove in order to effectively separate ethanol from the xylenes. Such a column, if needed, is expected to only be small in size and require simple carbon steel construction due to the relatively small amounts of xylenes present.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is:

1. A method for recovery of at least one alcohol from a dilute aqueous alcohol feed stream, said method comprising:
   a) providing a source of a dilute aqueous alcohol feed stream;
      wherein the dilute aqueous alcohol feed stream comprises at least one alcohol;
   b) substantially removing any solids from the dilute aqueous alcohol feed stream to form a feed stream substantially devoid of solids;
   c) circulating the feed stream substantially devoid of solids through a liquid-liquid extraction system comprising multiple equilibrium stages;
      wherein the feed stream substantially devoid of solids is contacted with a solvent that has an stronger affinity for the at least one alcohol than for water; and
      wherein the solvent is substantially immiscible with the feed stream substantially devoid of solids for a sufficient time to transfer at least a portion of the at least one alcohol into the solvent;
   d) recovering a raffinate phase substantially depleted in the at least one alcohol and an extract phase substantially enriched in the at least one alcohol;
   e) passing the extract phase to a recovery system in which the extract phase is subjected to microwave radiation;
      wherein the microwave radiation substantially heats the at least one alcohol but not the solvent to form a volatilized product comprising a substantially pure alcohol;
   f) recovering the volatilized product; and
   g) recycling the solvent to the liquid-liquid extraction system after the at least one alcohol has been volatilized.

2. The method of claim 1, further comprising:
   h) removing any residual water from the volatilized product to form a fuel-grade alcohol.

3. The method of claim 2, wherein the removing step comprises treatment of the volatilized product with zeolite molecular sieves.

4. The method of claim 1, wherein the at least one alcohol comprises ethanol.

5. The method of claim 1, wherein the at least one alcohol comprises butanol.

6. The method of claim 1, wherein a temperature of the dilute aqueous alcohol feed stream ranges from about 25° C. to about 100° C.

7. The method of claim 1, wherein a concentration of the dilute aqueous alcohol feed stream ranges from about 0.5 to about 20 weight percent alcohol.

8. The method of claim 1, wherein the liquid-liquid extraction system comprises at least one component selected from the group consisting of a mixer-settler, a spray column, a packed column, a perforated plate column, a baffled column, an agitated column, a centrifugal contactor and a membrane contactor.

9. The method of claim 8, wherein the membrane contactor comprises a plurality of hollow fibers.

10. The method of claim 9, wherein the feed stream substantially devoid of solids is fed into the interior (lumen) of each of the plurality of hollow fibers and the solvent is fed to the exterior (shell) of each of the plurality of hollow fibers.

11. The method of claim 1, wherein the solvent is selected from the group consisting of linear alkanes, linear alkenes, branched alkanes, branched alkenes, and aromatic hydrocarbons.

12. The method of claim 1, wherein the solvent comprises a non-polar primary component and a polar modifier;
   wherein the non-polar primary component is substantially microwave transparent; and
   wherein the polar modifier improves extraction of the at least one alcohol and more efficiently absorbs microwave radiation than the non-polar primary component.

13. The method of claim 12, wherein the non-polar primary component is selected from the group consisting of linear alkanes, linear alkenes, branched alkanes, branched alkenes, and aromatic hydrocarbons.

14. The method of claim 12, wherein the non-polar primary component is poly(dimethylsiloxane).

15. The method of claim 12, wherein the polar modifier is selected from the group consisting of a long chain alcohol, a long chain fatty acid, an ester of a long chain fatty acid, and an ether.

16. The method of claim 12, wherein the polar modifier comprises a naturally-occurring triglyceride;
wherein the naturally-occurring triglyceride is selected from the group consisting of soybean oil, corn oil, olive oil and castor oil.

17. The method of claim 12, wherein the polar modifier comprises greater than about 1 weight percent of the solvent.

18. The method of claim 1, wherein an extraction in the liquid-liquid extraction system is performed at a temperature between about 25° C. and about 100° C.

19. The method of claim 1, wherein a ratio of the solvent to the feed stream substantially devoid of solids ranges from about 0.1 to about 10.

20. The method of claim 1, wherein a pressure in the recovery system ranges from about 0.01 psia to about 20 psia.

21. The method of claim 1, wherein a frequency of the microwave radiation is about 2.45 GHz.

22. The method of claim 1, wherein the method is performed continuously.

23. The method of claim 1, wherein the method is performed batch-wise.

24. A method for recovery of at least one alcohol from a dilute aqueous alcohol feed stream, said method comprising:
a) providing a source of a dilute aqueous alcohol feed stream;
wherein the dilute aqueous alcohol feed stream comprises at least one alcohol;
b) substantially removing any solids from the dilute aqueous alcohol feed stream to form a feed stream substantially devoid of solids;
c) circulating the feed stream substantially devoid of solids through a hydrophobic, microporous membrane extraction system comprising a plurality of hollow fibers;
wherein the feed stream substantially devoid of solids is directed into the interior (lumen) of each of the plurality of hollow fibers and a solvent having a stronger affinity for alcohol than for water is directed to the exterior (shell) of each of the plurality of fibers; and
wherein the circulating step is performed for a sufficient time to transfer at least a portion of the at least one alcohol into the solvent;
d) recovering a raffinate phase substantially depleted in the at least one alcohol and an extract phase substantially enriched in the at least one alcohol;
e) passing the extract phase to a recovery system in which the extract phase is subjected to microwave radiation;
wherein the microwave radiation substantially heats the at least one alcohol but not the solvent to form a volatilized product comprising a substantially pure alcohol;
f) recovering the volatilized product; and
g) recycling the solvent to the hydrophobic, microporous membrane extraction system after the at least one alcohol has been volatilized.

25. The method of claim 24, further comprising:
h) recycling the raffinate phase for reuse in a fermentation process.

26. The method of claim 24, further comprising:
i) removing any residual water from the volatilized product to form a fuel-grade alcohol.

* * * * *